US00PP15636P2

(12) United States Plant Patent
den Haan

(10) Patent No.: US PP15,636 P2
(45) Date of Patent: Mar. 8, 2005

(54) *LEUCANTHEMUM* PLANT NAMED 'KIEDAI'

(50) Latin Name: *Chrysanthemum leucanthemum*
Varietal Denomination: Kiedai

(75) Inventor: Pieter den Haan, Steenbergen (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 10/822,987

(22) Filed: Apr. 13, 2004

(51) Int. Cl.[7] ..... A01H 5/00
(52) U.S. Cl. ..... Plt./284
(58) Field of Search ..... Plt./284

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Leucanthemum* plant named 'Kiedai', characterized by its upright and compact plant habit; dark green foliage; early and continuous flowering habit; daisy-type inflorescences with; white-colored ray florets and bright yellow-colored disc florets; and good garden performance.

1 Drawing Sheet

Botanical classification/cultivar designation: *Chrysanthemum leucanthemum* cultivar Kiedai.

BACKGROUND OF THE INVENTION

The present Invention relates to a new and distinct cultivar of *Leucanthemum* plant, botanically known as *Chrysanthemum leucanthemum* and hereinafter referred to by the name 'Kiedai'.

The new *Leucanthemum* is a product of a planned breeding program conducted by the Inventor in Steenbergen, The Netherlands. The objective of the breeding program is to create compact *Leucanthemum* cultivars that flower early and have good garden performance.

The new *Leucanthemum* originated from a cross-pollination made by the Inventor in the spring of 1995, in Steenbergen, The Netherlands, of a proprietary *Chrysanthemum leucanthemum* seedling selection identified as code number 92.2006, not patented, as the female, or seed, parent with a proprietary *Chrysanthemum leucanthemum* seedling selection identified as code number 91.1953, not patented, as the male, or pollen, parent. The new *Leucanthemum* was discovered and selected by the Inventor as a single flowering plant within the progeny of the stated cross-pollination grown in a controlled environment in Steenbergen, The Netherlands. The selection of this plant was based on its compact plant habit and early flowering.

Asexual reproduction of the new *Leucanthemum* by vegetative tip cuttings was first conducted in Steenbergen, The Netherlands in 1998. Asexual reproduction by cuttings has shown that the unique features of this new *Leucanthemum* are stable and reproduced true to type in successive generations.

SUMMARY OF THE INVENTION

The cultivar Kiedai has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Kiedai'.

These characteristics in combination distinguish 'Kiedai' as a new and distinct *Leucanthemum:*

1. Upright and compact plant habit.
2. Dark green-colored foliage.
3. Early and continuous flowering habit.
4. Daisy-type inflorescences with white-colored ray florets and bright yellow-colored disc florets.
5. Good garden performance.

Plants of the new *Leucanthemum* are not as compact and have larger Inflorescences than plants of the female parent selection. Plants of the new *Leucanthemum* are more compact and have smaller inflorescences than plants of the male parent selection.

Plants of the new *Leucanthemum* can be compared to plants of the *Leucanthemum* cultivar Kiemar, disclosed in U.S. Plant Pat. No. 12,978. In side-by-side comparisons conducted by the Inventor in Steenbergen, The Netherlands, plants of the new *Leucanthemum* differed from plants of the cultivar Kiemar in the following characteristics:

1. Plants of the new *Leucanthemum* grew faster and stronger than plants of the cultivar Kiemar.
2. Plants of the new *Leucanthemum* had smaller inflorescences than plants of the cultivar Kiemar.

BRIEF DESCRIPTION OF THE PHOTOGRAPHS

The accompanying colored photographs illustrate the overall appearance of the new *Leucanthemum* showing the colors as true as it is reasonably possible to obtain in colored reproductions of this type. Colors in the photographs may differ from the color values cited in the detailed botanical description which accurately describe the colors of the new *Leucanthemum.*

The photograph at the bottom of the sheet comprises a side perspective view of a typical flowering plant of 'Kiedai'.

The photograph at the top of the sheet comprises a close-up view of typical inflorescences and leaves of 'Kiedai'.

DETAILED BOTANICAL DESCRIPTION

The cultivar Kiedai has not been observed under all possible environmental conditions. The phenotype may vary somewhat with variations in environment such as temperature and light intensity without, however, any variance in genotype. The aforementioned photographs and following observations, measurements and comparisons describe plants grown in Lompoc, Calif., under commercial practice during the winter in a polycarbonate-covered greenhouse with day temperatures about 18 to 24° C., night temperatures about 16 to 18° C. and light levels about 4,000 to 8,000 foot-candles. Unrooted cuttings were directly planted in 10-cm containers and had been growing for about seven weeks when the photographs and description were taken.

In the following description, color references are made to The Royal Horticultural Society Colour Chart, 1995 Edition, except where general terms of ordinary dictionary significance are used.

Botanical classification: *Chrysanthemum leucanthemum* cultivar Kiedai.

Parentage:

*Female, or seed, parent.*—Proprietary *Chrysanthemum leucanthemum* seedling selection identified as code number 92.2006, not patented.

*Male, or pollen, parent.*—Proprietary *Chrysanthemum leucanthemum* seedling selection identified as code number 91.1953, not patented.

Propagation:

*Type.*—Terminal tip cuttings.

*Time to initiate roots.*—About three weeks at 18° C.

*Time to produce a rooted cutting.*—About four weeks at 18° C.

*Root description.*—Fine, fibrous; white in color.

*Rooting habit.*—Freely branching; moderately dense.

Plant description:

*Appearance.*—Compact and upright plant habit; narrow inverted triangle. Freely basal branching with about five lateral branches per plant. Moderately vigorous.

*Plant height.*—About 26 cm.

*Plant width.*—About 9 cm.

*Lateral branches.*—Length: About 25 cm. Diameter: About 3.5 mm. Internode length: About 2.5 cm. Strength: Strong. Texture: Glabrous, smooth; longitudinally ridged. Color: 144A; longitudinal stripes, 59A.

*Foliage description.*—Arrangement: Alternate, simple; sessile. Length: About 5.5 cm. Width: About 1.8 cm. Shape: Lanceolate. Apex: Acute. Base: Attenuate; clasping. Margin: Irregularly dentate. Texture, upper and lower surfaces: Smooth, glabrous; slightly glandular. Venation pattern: Pinnate. Color: Developing foliage, upper and lower surfaces: 146A. Fully expanded foliage, upper surface: 147A. Fully expanded foliage, lower surface: 147B. Venation, upper surface: 146B. Venation, lower surface: 146A.

Inflorescence description:

*Appearance.*—Daisy-type inflorescence form with ligulate-shaped ray florets. Inflorescences borne on terminals above foliage. Disk and ray florets arranged acropetally on a capitulum. Inflorescences persistent. Not fragrant. Typically one terminal inflorescence and two lateral inflorescence per lateral branch.

*Flowering response.*—Under natural conditions, plants flower in the spring. Under greenhouse conditions, plant flower year-round. Flowering continuous. Early flowering, plants begin to flower about four weeks after planting cuttings.

*Inflorescence longevity.*—Inflorescences maintain good color and substance for about 10 to 14 days on the plant.

*Inflorescence bud.*—Height: About 1 cm. Diameter: About 1.2 cm. Shape: Ovoid. Color: 157A.

*Inflorescence size.*—Diameter: About 6.5 cm. Depth (height): About 1.8 cm. Diameter of disc: About 2 cm. Receptacle diameter: About 2.1 cm. Receptacle height: About 1 cm.

*Ray florets.*—Shape: Ligulate with longitudinal ridges. Orientation: Initially upright, then about 90° from vertical or perpendicular to peduncle. Aspect: Initially incurved, then reflexed. Length: About 3 cm. Width: About 1 cm. Apex: Emarginate. Base: Acute; short corolla tube. Margin: Entire. Texture, upper and lower surfaces: Smooth, glabrous; satiny. Number of ray florets per inflorescence: About 28 arranged in about two rows. Color: When opening, upper and lower surfaces: 155A. Fully opened, upper and lower surfaces: 155D; towards the base, 146C.

*Disc florets.*—Arrangement: Massed at center of receptacle. Shape: Tubular, elongated. Apex: Five-pointed. Length: About 7 mm. Width, at apex: About 1 mm. Width, at base: Less than 1 mm. Number of disc florets per inflorescence: About 450. Color, immature: 145B. Color, mature: Apex: 11A. Midsection: 145C. Base: 146C.

*Phyllaries.*—Quantity/arrangement: About 42 in about three imbricate whorls. Shape: Lanceolate. Apex: Acute. Base: Truncate. Margin: Entire, membranous. Texture, upper and lower surfaces: Smooth, glabrous. Color, upper and lower surfaces: 144A.

*Peduncles.*—Length, terminal peduncle: About 9 cm. Length, second peduncle: About 8 cm. Length, third peduncle: About 2.3 cm. Diameter: About 2.5 mm. Aspect: Terminal, upright; second and third, outward. Strength: Strong. Texture: Smooth; longitudinally ridged. Color: 137A.

*Reproductive organs.*—Androecium: Present on disc florets only. Stamen quantity: Five. Anther shape: Ovoid. Anther length: Less than 1 mm. Anther color: 14A. Pollen amount: Scarce. Pollen color: 14A. Gynoecium: Present on both ray and disc florets. Pistil quantity: One. Pistil length: About 5 mm. Stigma shape: Two-parted. Stigma color: 14A. Style length: About 2 mm. Style color: 154C. Ovary color: 145A.

*Seed/fruit.*—Seed and fruit production has not been observed.

Disease/pest resistance: Resistance to pathogens and pests common to *Leucanthemums* has not been observed on plants grown under commercial greenhouse conditions.

Garden performance: Good garden performance; plants of the new *Leucanthemum* have been observed to be tolerant to rain, wind and temperatures ranging from 5 to 35° C.

It is claimed:

1. A new and distinct cultivar of *Leucanthemum* plant named 'Kiedai', as illustrated and described.

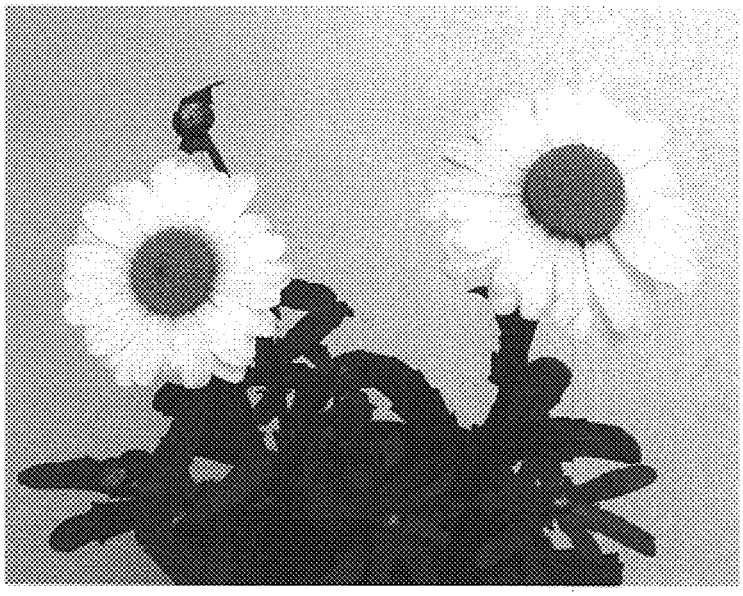
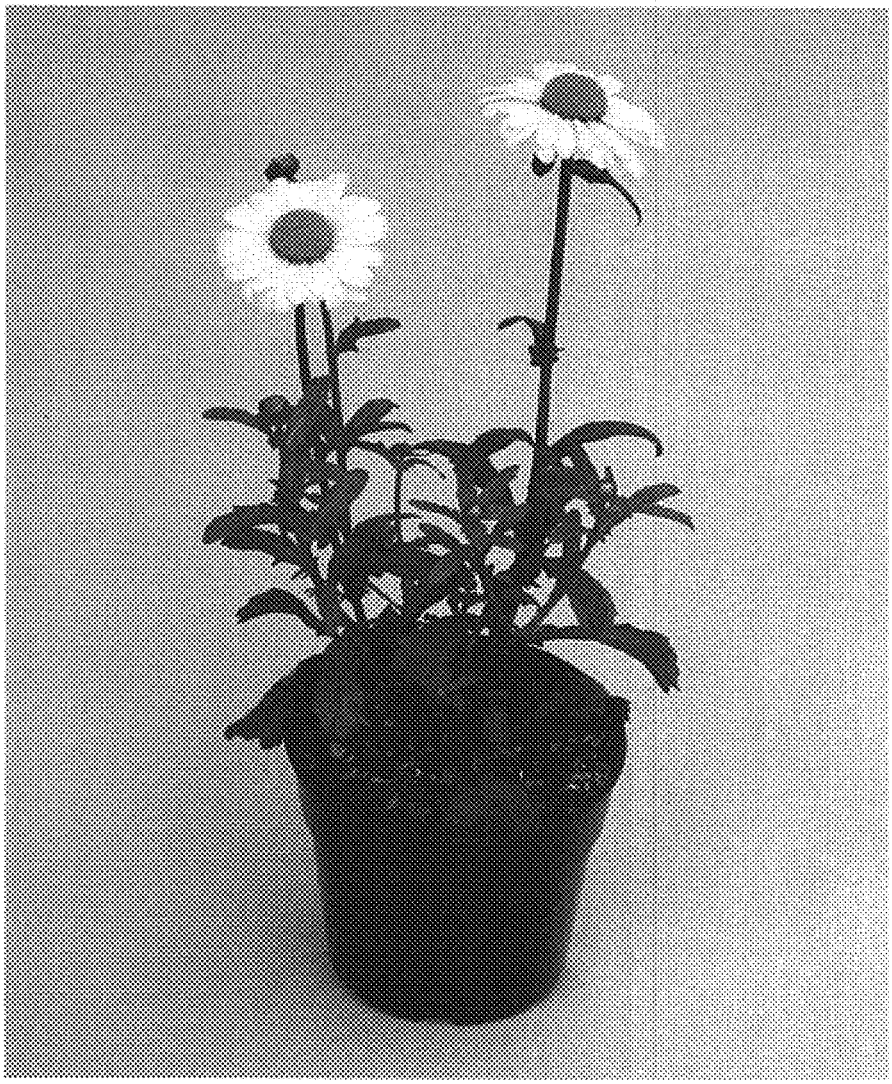

* * * * *